(12) United States Patent
Bessard et al.

(10) Patent No.: US 6,469,178 B2
(45) Date of Patent: Oct. 22, 2002

(54) PROCEDURE FOR PRODUCING FORMYLIMIDAZOLES

(75) Inventors: Yves Bessard, Sierre; Josef Heveling, Naters, both of (CH)

(73) Assignee: Lonza AG, Basel (CH)

( * ) Notice: Subject to any disclaimer, the term of this patent is extended or adjusted under 35 U.S.C. 154(b) by 0 days.

(21) Appl. No.: 10/005,283

(22) Filed: Dec. 5, 2001

(65) Prior Publication Data

US 2002/0045760 A1 Apr. 18, 2002

Related U.S. Application Data

(63) Continuation of application No. 09/820,394, filed on Mar. 29, 2001, now abandoned, which is a continuation of application No. 09/554,308, filed as application No. PCT/EP98/07322 on Nov. 10, 1998, now abandoned.

(30) Foreign Application Priority Data

Nov. 14, 1997 (CH) .............................................. 2638/97
Nov. 27, 1997 (CH) .............................................. 2738/97

(51) Int. Cl.$^7$ ........................................... C07D 233/22
(52) U.S. Cl. ................................................. 548/333.5
(58) Field of Search ...................................... 548/333.5

(56) References Cited

U.S. PATENT DOCUMENTS

| | | | |
|---|---|---|---|
| 5,336,779 A | 8/1994 | Yamamoto et al. | 548/333.5 |
| 5,917,051 A | 6/1999 | Heveling et al. | 548/333.5 |

*Primary Examiner*—Joseph K. McKane
*Assistant Examiner*—Joseph Murray
(74) *Attorney, Agent, or Firm*—Mary E. McCarthy; Charles M. Kinzig

(57) ABSTRACT

A new process for the catalytic conversion of hydroxymethyl imidazoles to formylimidazoles is described. The reaction takes place in the presence of a peroxide. Formylimidazoles are important intermediate products for pharmaceutical substances.

7 Claims, No Drawings

PROCEDURE FOR PRODUCING FORMYLIMIDAZOLES

This is a continuation of application Ser. No: 09/820,394 filed Mar. 29, 2001 now abandoned which is a continuation Ser. No. 09/554,308 filed May 11, 2000, now abandoned, which is a 371 of Intern. App. No. PCT/EP98/07322 filed Nov. 10, 1998, which claims the benefit of Switzerland application Nos: 2738/97 filed Nov. 27, 1997 and 2638/97 filed Nov. 14, 1997.

This invention concerns a new procedure for producing formyl imidazoles of the general formula

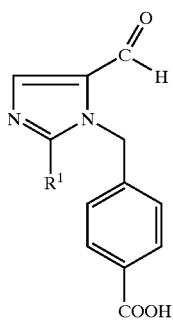

(I)

in which $R^1$ means an alkyl group, by catalytic oxidation of hydroxy methyl imidazoles of the general formula

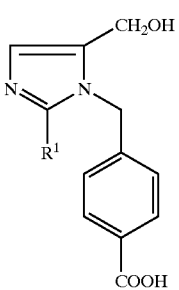

(II)

in which $R^1$ has the meaning given above.

Formyl imidazoles are important intermediate products, for example, for the production of pharmaceutical substances such as diuretics or antihypertensives (WO-A 92/20651). Several procedures have previously been known for producing formyl imidazoles. In CH-A 685496, a procedure is described in which the catalytic oxidation of hydroxy methyl imidazoles to formyl imidazoles is performed in the presence of noble metal catalysts such as platinum bismuth, platinum black, platinum or palladium on activated charcoal with oxygen insufflation.

The task of the invention was therefore to make available an economical improved procedure for producing formyl imidazoles.

In this invention, this task is solved by the procedure defined in claim 1.

In claim 1, hydroxy methyl imidazoles of the general formula

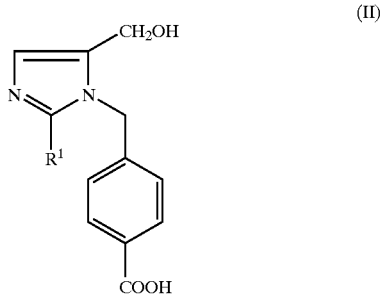

(II)

in which $R^1$ has the meaning given above, are catalytically oxidized in the presence of a noble metal catalyst and a peroxide to formyl imidazoles of the general formula

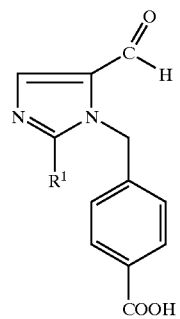

(I)

in which $R^1$ has the meaning given above.

$R^1$ has the meaning of hydrogen or an alkyl group, and more particularly a straight-chained or ramified alkyl group with 1 to 6 C atoms. Specifically, this may be methyl, ethyl, propyl, isopropyl, butyl, isobutyl, tert-butyl, pentyl and its isomers as well as hexyl and its isomers. The preferred meaning $R^1$ is butyl.

Hydroxy methyl imidazoles can be readily produced as starting compounds as specified, for example, in WO-A 92/20651 or in E. F. Godefroi et al., Trav. Chim. Receuil Pays-Bas, 91, 1383 (1972).

Platinum, palladium, rhodium or gold can be used as the noble metal catalyst. The noble metal is appropriately used in combination with metals such as, for example, bismuth, lead, cerium or indium as the second component. The preferred catalysts are platinum/bismuth or platinum/lead.

The noble metal catalyst is used by itself or bound to a vehicle such as, for example, activated charcoal, silicon dioxide, aluminum dioxide, silicon-aluminum dioxide, zirconium oxide or titanium oxide. It is preferably bound to activated charcoal.

Noble metal catalysts bound to activated charcoal can be commercially obtained, for example, from Degussa.

The appropriate percentage of the noble metal bound to a vehicle is between 0.1 and 15% by weight, and preferably between 0.5 and 7% by weight, relative to the vehicle material.

The noble metal catalyst is preferably used in an amount of 0.05 to 1.0 mol % noble metal base relative to hydroxy methyl imidazole, and an amount of 0.1 to 0.4 mol % noble metal base relative to hydroxy methyl imidazole is especially preferred.

Organic or inorganic peroxides are used as peroxides. Hydrogen peroxide, perborates, a percarboxylic acid, tert-butyl hydroperoxide, cumol hydroperoxide, perbenzoic acid, m-chloroperbenzoic acid, monoperphthalic acid or peracetic acid are well suited, for example. Hydrogen peroxide used in a 10% to 30% aqueous solution is particularly suitable.

The catalytic oxidation takes place appropriately in the presence of water, a water-miscible solvent or mixtures thereof, in an alkaline milieu.

Particularly suitable water-miscible solvents are for example, alcohols or carboxylic acids with 1 to 6 C atoms or ketones such as, for example, acetone or methyl ethyl ketone.

Mixtures of water and water-miscible solvents are preferably used. It has proven to be advantageous if the water used is adjusted to be alkaline, by the appropriate addition of an alkali hydroxide, an alkali carbonate or an alkali acetate. Alkali hydroxide is preferably used in the ratio 1:0.05 to 5, and preferably 1:1 to 3, relative to the mol amount used of the hydroxy methyl imidazole of general formula II.

The catalytic oxidation is appropriately performed at a temperature of 20° to 120° C., preferably at 50°–80° C.

After the standard peroxide dosing time of 2–3 hours, the compound of general formula I can be isolated in the standard manner after a sufficient secondary reaction time.

The product is isolated by appropriate crystallization and filtration. The catalyst used can be used several times with no loss of activity.

EXAMPLES

Example 1

Production of 4-[(2-butyl-5-formyl-1H-imidazo-1-yl)methyl]benzoic acid 9.5 g (33 mmol) 4-[(2-butyl-5-hydroxymethyl-1H-imidazo-1-yl)methyl]benzoic acid, 40 ml water, 10 ml methanol, 4.2 g (105 mmol) NaOH and 0.92 g 5% platinum and 5% bismuth on activated charcoal (containing 60% water) are placed in a 100-ml flask at room temperature and heated to 60° C. 6.6 g (39 mmol) 20% aqueous $H_2O_2$ solution were added to this suspension at 60° C. over 60 minutes and the mixture was then converted with HPLC. 6.6 g (39 mmol) 20% aqueous $H_2O_2$ solution were again added over 60 minutes. 1.7 g (10 mmol) 20% aqueous $H_2O_2$ solution were then added over 20 minutes (conversion >90%). The mixture was cooled to room temperature. After acidification to pH 6.0 with 17.6 ml HCl (15%), the product was preciptated. It was cooled to 2° C., filtered, washed with 2×20 ml water, and dried at room temperature at 15 mbar. 7.2 g (70%) of yellow 4-[(2-butyl-5-formyl-1H-imidazo-1-yl)methyl]benzoic acid (HPLC content 95%) were obtained.

Melting point: 144–146° C.

| $^1$H-NMR (DMSO-$_{d6}$, 400 MHz)δ: | 12.9 (1 H, s); |
| | 9.65 (1 H, s); |
| | 7.94 (1 H, s); |
| | 7.90 (2 H, d); |
| | 7.11 (2 H, d); |
| | 5.65 (2 H, s); |
| | 2.63 (2 H, t); |
| | 1.54 (2 H, pent); |
| | 1.36 (2 H, hex); |
| | 0.79 (3 H, t). |

What is claimed is:

1. A process for producing formylimidazoles of the formula (I):

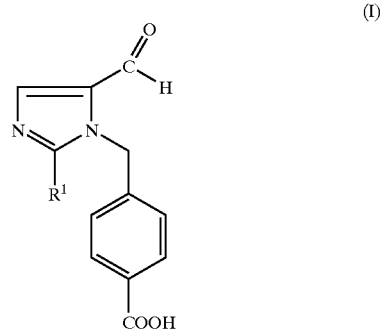

in which $R^1$ is $C_{1-6}$ alkyl, which comprises catalytic oxidation of hydroxymethyl imidazoles of the general formula (II):

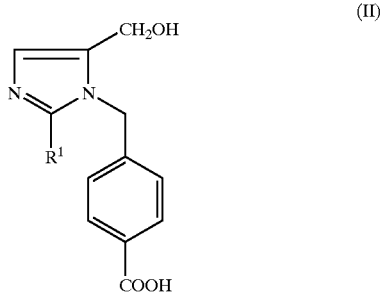

in which $R^1$ is defined above, in the presence of a noble metal catalyst, wherein the catalytic oxidation takes place in the presence of a peroxide.

2. The process according to claim 1 wherein $R^1$ is butyl.

3. The process according to claim 1 wherein the noble metal catalyst is a platinum/bismuth catalyst or a platinum/lead catalyst.

4. The process according to claim 1 wherein the peroxide is hydrogen peroxide.

5. The process according to claim 1 wherein the catalytic oxidation is performed in the presence of water, a water-miscible solvent or mixtures thereof, in an alkaline medium.

6. The process according to claim 5 wherein the alkaline medium is obtained by adding an alkali hydroxide, an alkali carbonate or an alkali acetate to the reaction mixture.

7. The process according to claim 1 wherein the reaction is performed at a temperature of 20°–120° C.

* * * * *